United States Patent [19]
Spievack

[11] Patent Number: 6,053,918
[45] Date of Patent: Apr. 25, 2000

[54] APPARATUS AND METHOD FOR FASTENING AN INTRAMEDULLARY NAIL TO A BONE

[75] Inventor: Alan R. Spievack, Cambridge, Mass.

[73] Assignee: General Orthopedics, Cambridge, Mass.

[21] Appl. No.: 08/328,443

[22] Filed: Oct. 25, 1994

[51] Int. Cl.[7] .............................. A61B 17/72; A61B 17/17
[52] U.S. Cl. .............................. 606/64; 606/98; 606/104; 606/77; 606/96
[58] Field of Search .................................. 606/62, 64, 96, 606/98, 67

[56] References Cited

U.S. PATENT DOCUMENTS

| | | |
|---|---|---|
| 4,016,874 | 4/1977 | Maffei et al. . |
| 4,281,649 | 8/1981 | Derweduwen . |
| 4,621,628 | 11/1986 | Brudermann . |
| 4,622,959 | 11/1986 | Marcus . |
| 4,781,181 | 11/1988 | Tanguy . |
| 4,943,291 | 7/1990 | Tanguy . |
| 5,057,110 | 10/1991 | Kranz et al. .............................. 606/67 |

FOREIGN PATENT DOCUMENTS

| | | | |
|---|---|---|---|
| 218492 | 4/1987 | European Pat. Off. .................. | 606/64 |
| 4033280 | 10/1991 | Germany .................................. | 606/64 |

OTHER PUBLICATIONS

Synthes (U.S.A.), Marketing Brochure, "The Large Cannulated Screw System," (1989) (consisting of 6 pages).

Synthes (U.S.A.), Marketing Brochure, "The Small Cannulated Screw System," (1989) (consisting of 6 pages).

*Primary Examiner*—Gary Jackson
*Assistant Examiner*—David O. Reip
*Attorney, Agent, or Firm*—Hamilton, Brook, Smith & Reynolds, P.C.

[57] ABSTRACT

A cannulated screw is employed to fasten an intramedullary nail to a bone of a patient. A guide is disposed within the intramedullary nail and registered with a preformed securing hole in the nail. Preferably, the guide is fabricated from a bio-absorbable material such as polyglycolic acid and fixedly registered to the distal securing holes. A flexible drill shaft is directed to the selected securing hole by the guide. The drill is operated to drill through the bone cortex and soft tissue of the patient to exit the skin of the patient. A cannulated fixation screw is fitted over the exposed drill bit and is then driven into the patient, guided by the drill bit back to the selected securing hole. The drill bit is then extracted and the cannulated screw is driven through the intramedullary nail into the opposite cortex of the bone. After all of the fixation screws have been placed, the intramedullary nail is fastened to the bone.

58 Claims, 15 Drawing Sheets

APPARATUS AND METHOD FOR FASTENING AN INTRAMEDULLARY NAIL TO A BONE

BACKGROUND OF THE INVENTION

Fractures in long bones of the thigh and lower leg can be assisted in the repair process by inserting an intramedullary nail through the intramedullary canal of the bone. The fractured bone segments are aligned and then the intramedullary canal of each bone segment is reamed to create a bored canal. The intramedullary nail is then inserted into the bored canal from a proximal bone segment through to a distal bone segment. The nail is secured to the proximal and distal bone segments using screws or pins. After the intramedullary nail is secured to the bone, the fractured segments are fixed in position relative to each other such that new bone cells grow in the fractured areas. After the bone is healed, the intramedullary nail is removed from the bone.

The intramedullary nail has a plurality of preformed securing holes at the proximal and distal ends of the nail. However, the exact position of the securing holes in the nail relative to the bone and the body after insertion is not accurately known. A number of glide devices have been developed to locate the securing holes to permit drilling of a bore from the outside of the body through the securing holes and into the opposing cortex sections of the bone. Prior art guides have operated from both inside the nail and external to the body. The most difficult securing holes to locate are at the distal end of the nail.

SUMMARY OF THE INVENTION

Briefly, the invention resides in an apparatus, a system and method for fastening an intramedullary nail to a bone. The fastening is initiated by boring a pilot hole through a bone from within a hollow intramedullary nail having preformed securing holes. A guide is disposed within the intramedullary nail to determine the position of a selected securing hole.

Preferably, the guide is fixedly registered to the distal securing holes. The guide is fabricated from a bio-absorbable material such as polyglycolic acid (PGA). As such, the guide can be left in the body, drilled through or otherwise damaged or destroyed without causing harm to the patient. In particular, the intramedullary nail is adapted to receive a nail tip having the fixed guide.

A flexible-shafted drill is passed down the nail and is guided through a funnel cavity to drill the pilot hole through the bone and soft tissue on the lateral aspect of the bone. The surgeon then passes a center cannulated drill screw or pin over the flexible drill shaft and drives the screw through the soft tissue against the bone. The flexible drill is then withdrawn and the surgeon drives the screw through the bone and nail complex, interlocking the nail and bone with the screw. A jig is preferably used to locate the other securing holes.

After the intramedullary nail is placed in the bone, a guide member can alternatively be passed down the center of the hollow nail. A handle and rod are used to maneuver and position the guide member within the nail. A spring-loaded ball detent snaps into a securing hole in the nail. This positions a drill exit opening registered to a selected securing hole, which is displaced relative to the positioning ball by a known amount. Unlike the fixed guide, the guide member must be removed before the screw can be driven through the nail.

The above and other features of the invention, including various novel details of construction and combination of parts, will now be more particularly described with reference to the accompanying drawings and pointed out in the claims. It will be understood that the particular intramedullary bone drill embodying the invention is shown by illustration only and not as a limitation of the invention. The principle and features of this invention may be employed in varied and numerous embodiments without departing from the scope of the invention.

DETAILED DESCRIPTION OF PREFERRED EMBODIMENTS OF THE INVENTION

Figure 1:
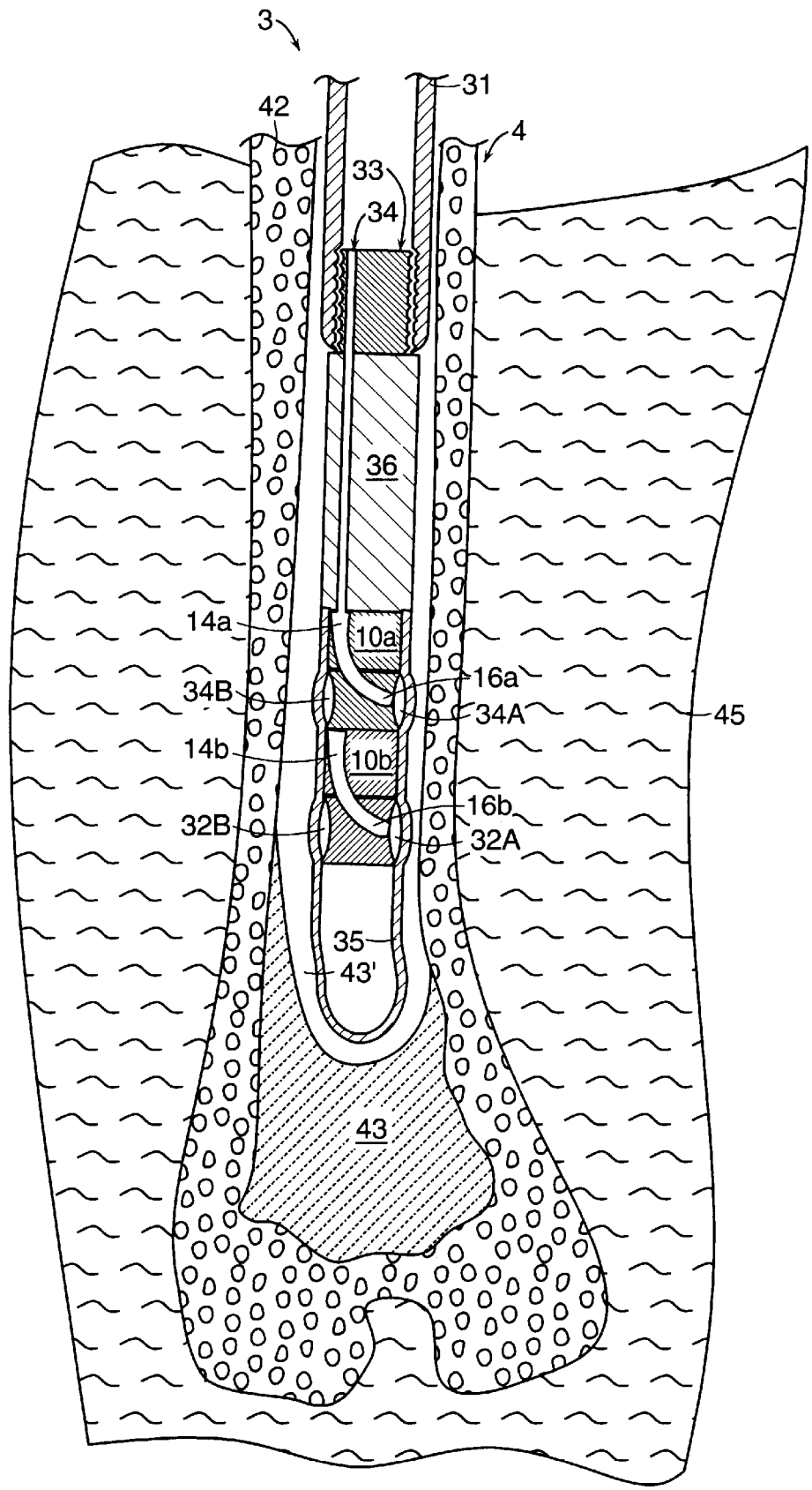
FIG. 1 is a foreshortened cross sectional schematic diagram of an integrated guide and nail apparatus disposed within an intramedullary canal of a femur bone.

FIG. 1 is a foreshortened cross sectional schematic diagram of an integrated guide and nail apparatus in accordance with the invention. As illustrated, the integrated guide and nail apparatus is disposed within an intramedullary canal 43 of a femur bone 42. At least one guide body 10a, 10b having a funnel cavity 14a, 14b is fixed within an intramedullary nail 3. An exit opening 16a, 16b of the funnel cavity 14a, 14b registers with a respective securing hole 34A, 32A of the nail 3. The integrated guide body 10a, 10b is preferably fabricated from polyglycolic acid (PGA) or another bioabsorbable suture material. Because the integrated guide bodies 10a, 10b are fixedly registered to the securing holes 34A, 32A, the surgeon does not manually manipulate the guide bodies 10a, 10b, which reduces the time needed for surgery in comparison with prior art methods.

As illustrated, each pair of distal securing holes 32A–32B, 34A–34B is associated with a respective guide body 10b, 10a. Preferably, the guide bodies 10a, 10b are supplied with an interchangeable intramedullary nail tip 35. The nail tip 35 is threaded onto a nail body 31 at a coupling 33. Examples of nail tips that can be suitably adapted for use with the invention are disclosed in U.S. patent application Ser. No. 08/200,073 filed Feb. 22, 1994 and entitled "Bone and Tissue Lengthening Device" by Alan Spievack, the teachings of which are incorporated herein by reference in their entirety As illustrated, the guide bodies 10a, 10b include a respective funnel cavity 14, 14b. The nail tip 35 or portion of the nail 3 can also or alternatively include an aperture 34 sized to correspond with a drill shaft 2 (FIG. 4) and to guide the drill shaft 2 to the exit opening 16. For example, instead of being a thin-walled hollow tube, the nail 3 or nail tip 35 can include a solid member 36 with the longitudinal aperture 34 bored therein. Such an aperture is preferably eccentric with the cross section of the nail to facilitate guiding the drill shaft 2 through the guide body 14.

Figure 2A:
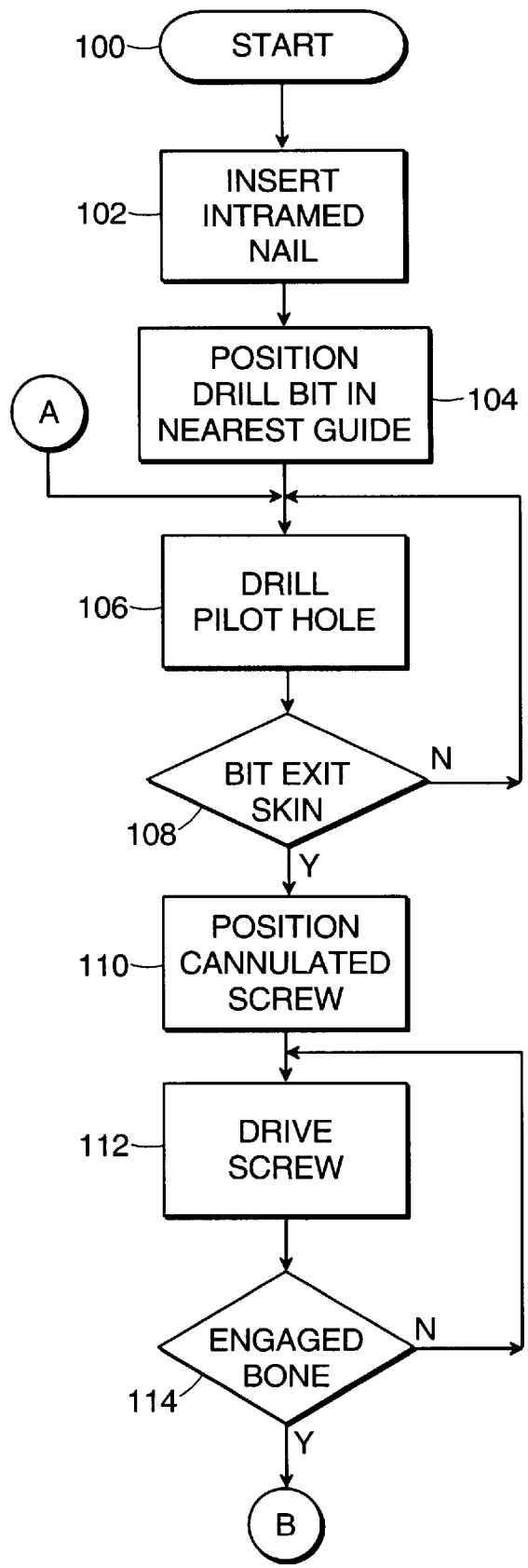
FIGS. 2A–2B are, when combined, a flowchart of a preferred surgical method of using the integrated guide and nail apparatus of FIG. 1.
Figure 2B:
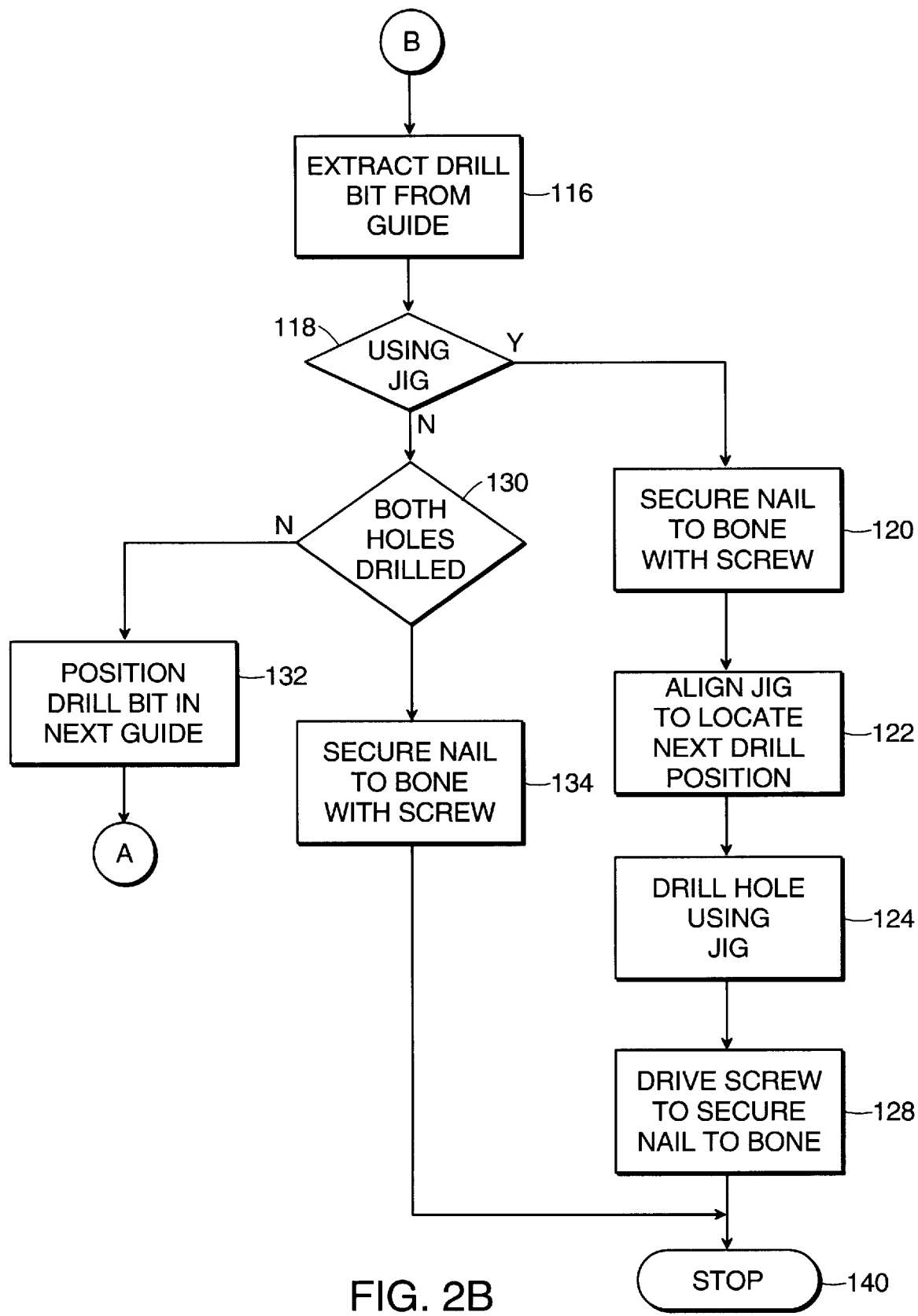

FIGS. 2A–2B are, when combined, a flowchart of a preferred surgical method of using the integrated guide and nail apparatus of FIG. 1. At step 100, the surgeon begins the method after boring the intramedullary canal with any suitable technique known in the art. A surgical method in accordance with the invention is illustrated in more detail by FIGS. 3–9.

Figure 3:
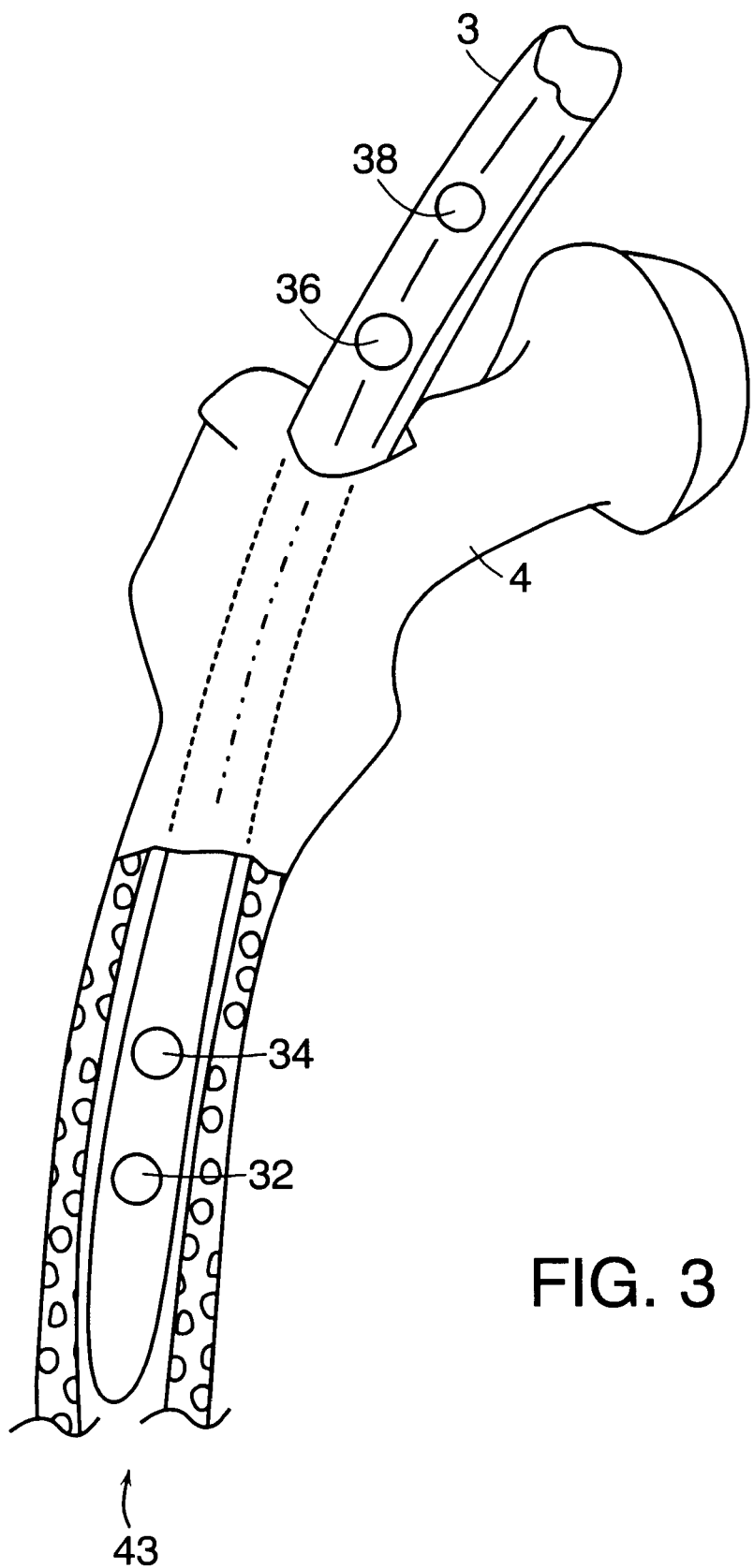
FIG. 3 is a schematic perspective diagram of an intramedullary nail being inserted into a human femur with a section of the femur being broken away.

At step 102 of FIG. 2A, an intraiedullary nail 3 having the integrated guides 10a, 10b is inserted into the bored canal. FIG. 3 is a schematic perspective view of an intramedullary nail 3 being inserted into the bored intramedullary canal 43 of a bone 4, with a portion of the bone broken away. As illustrated, the bone is a human femur but the procedure can be performed on other long bones as well. As illustrated, the intramedullary nail 3 has a clover-leaf cross section and includes four preformed securing holes 32, 34, 36, 38. These securing holes 32, 34, 36, 38 have a respective opening on each side of the intramedullary nail 3. It is understood that the intramedullary nail 3 can have other cross sections and other arrangements of securing holes.

Figure 4:
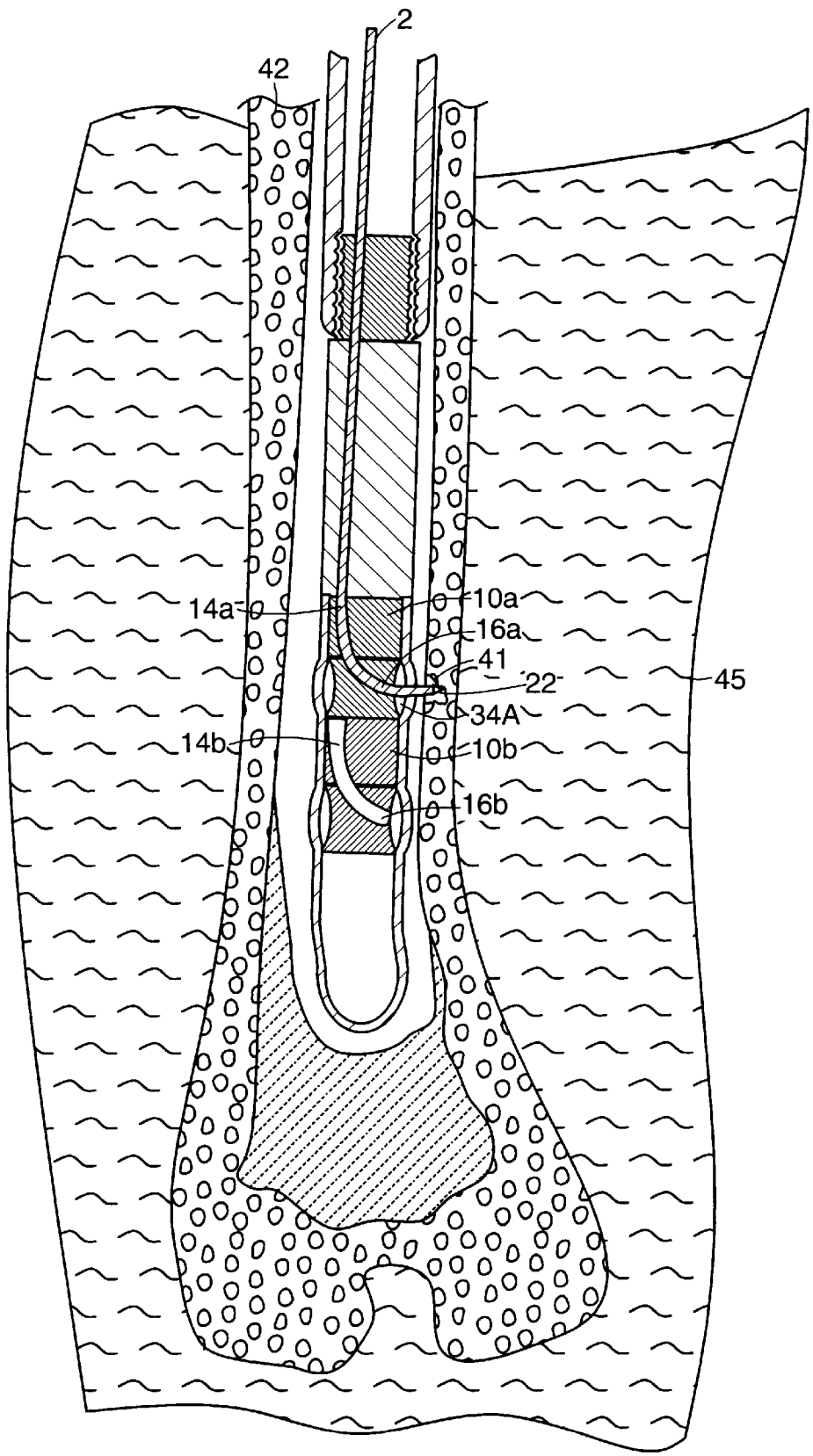
FIG. 4 is a foreshortened cross sectional schematic diagram of a pilot hole being bored through the bone cortex from the intramedullary canal using the integrated guide of FIG. 1.

At step 104 of FIG. 2A, the surgeon passes a flexible speed drill shaft into the funnel cavity 14a of the nearest (most proximate) guide 10a. At steps 106 and 108, the surgeon attaches the speed drill to a power handle and drills laterally out through the cortex of the bone and soft tissue of the body. The flexible drill shaft is guided by the funnel cavity 14a to the bone cortex through the securing hole 32A. FIG. 4 is a foreshortened cross sectional view of a pilot hole 41 being bored through the bone cortex 42 from the intramedullar, canal using the integrated guide 10 of FIG. 1. As illustrated, the flexible drill shaft 2 is guided by the funnel cavity 14 to the bone cortex 42 through the selected securing hole 32A. The drive shaft 2 must be flexible over at least a portion of its length from the drill bit 22 equal to the distance from the intramedullary canal through the skin of the patient.

Figure 5:
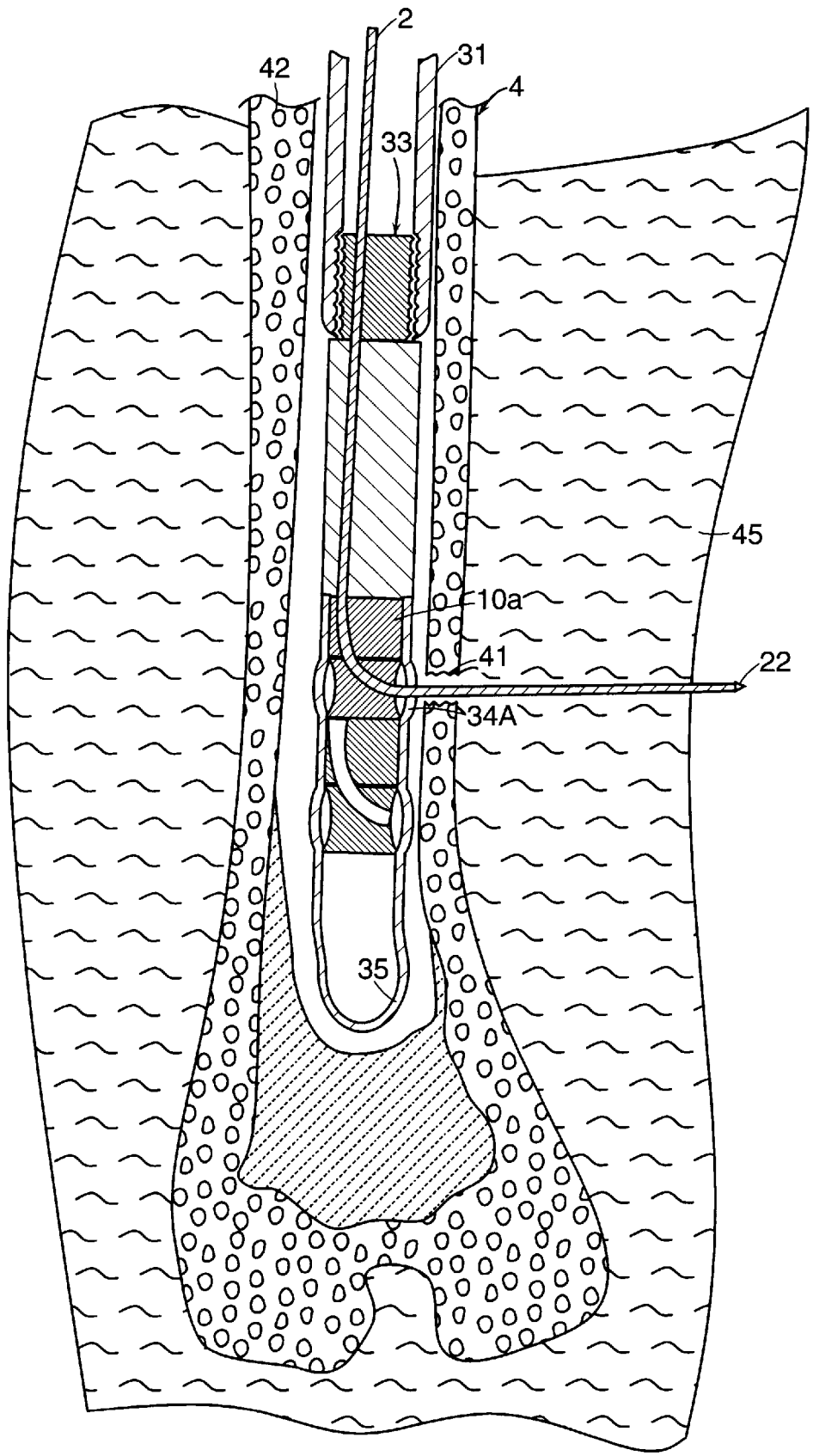
FIG. 5 is a foreshortened cross sectional schematic diagram illustrating a drill bit of FIG. 4 extending through a thigh.

The surgeon continues to drill until the drill bit exits the patient's skin. FIG. 5 is a foreshortened cross sectional schematic diagram of the drill bit 22 extending through the thigh 45 of a patient. After boring through the bone cortex, the drill bit 22 continues to drill through the soft tissue of the thigh 45. As illustrated, the drill bit 22 protrudes through the skin. The drill bit is now ready to receive a cannulated drill screw.

Figure 6:
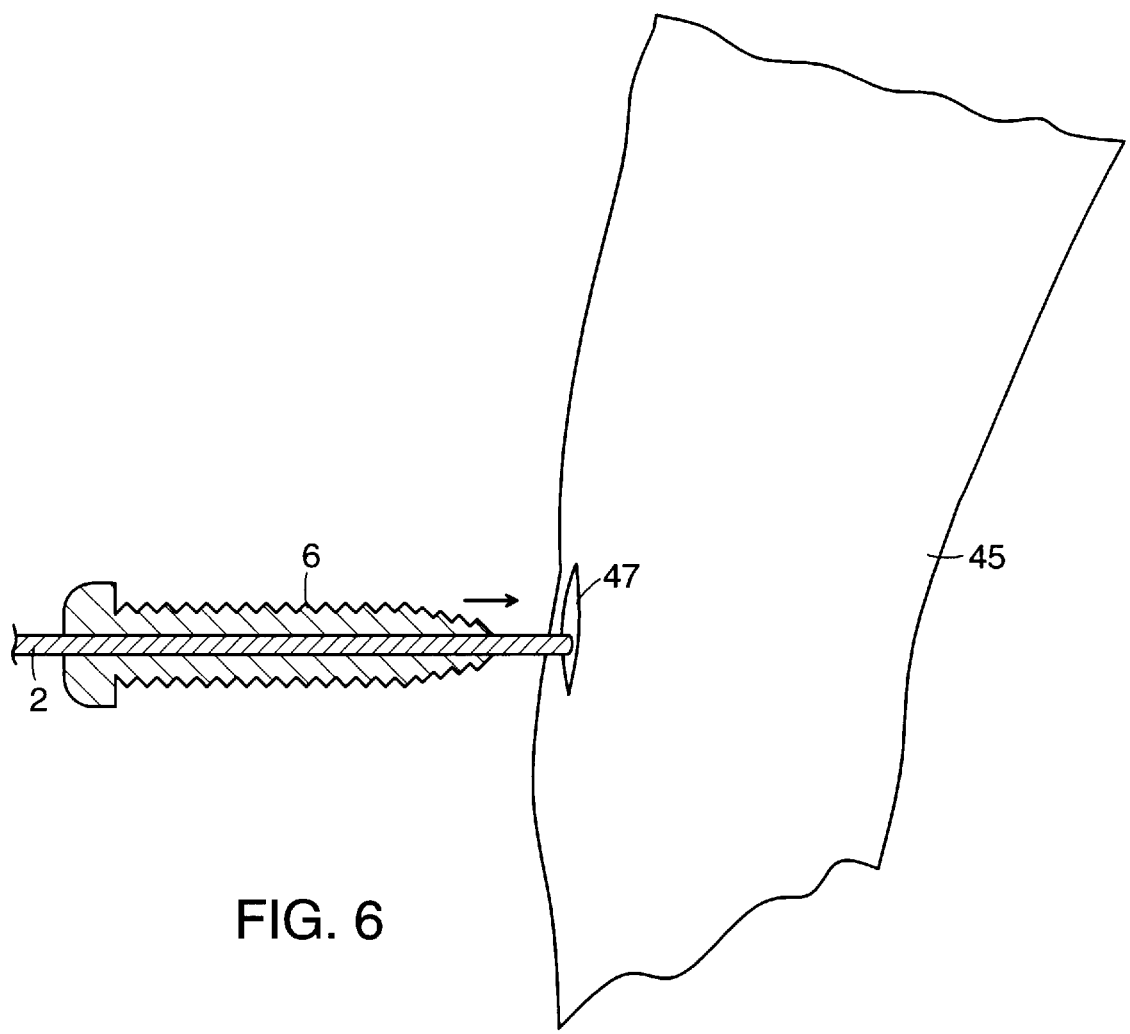
FIG. 6 is a foreshortened cross sectional schematic diagram illustrating the insertion of: a cannulated screw over the drill bit of FIG. 5.

At step 110 of FIG. 2A, the surgeon makes a small opening with a scalpel (e.g., a No. 11 blade) and places a cannulated drill screw (or pin) over the speed drill bit and attaches a power drive mechanism to the drill screw. FIG. 6 is a foreshortened cross sectional schematic diagram illustrating an incision 47 made in the skin of the thigh 45 where the flexible drill shaft 42 extends from the thigh 45. Illustrated is a center cannulated drill screw 6 fitted over the drill shaft 2, which guides the screw 6 through the leg to the bone. Such cannulated drill screws are commercially available from Synthes (USA) of Paoli, Pa.

Figure 7:
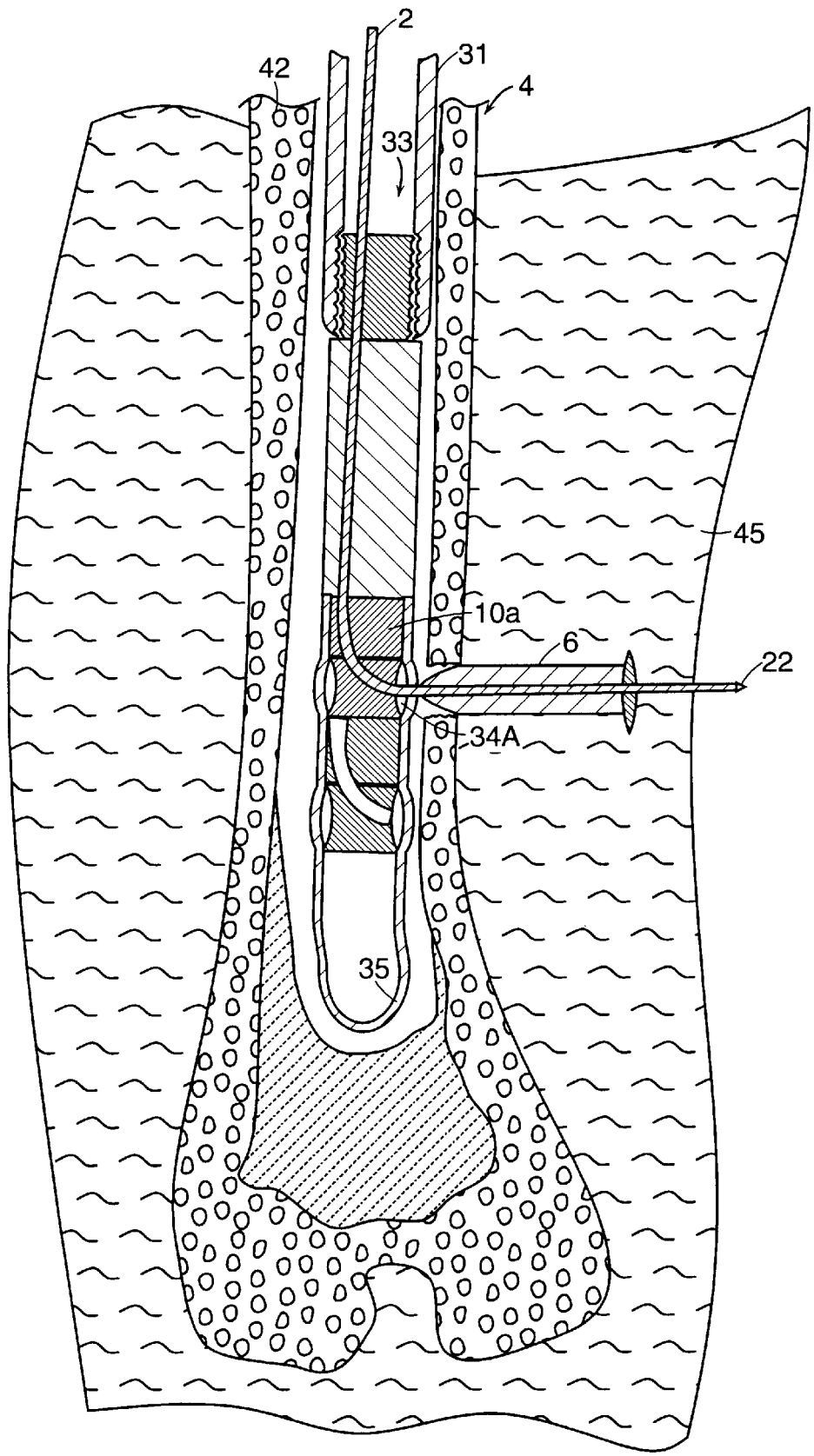
FIG. 7 is a foreshortened cross sectional schematic diagram of the cannulated screw of FIG. 6 engaging the bone.

At step 112 of FIG. 2A, the cannulated dill screw is driven through the soft tissue to the bone following the flexible drill shaft 2 as shown by the arrow in FIG. 6. The surgeon then begins to drive the screw into the lateral cortex of the bone. As soon as the drill screw firmly engages the bone (step 114 of FIG. 2A), the surgeon extracts the drill shaft from the drill screw (step 116 of FIG. 2B). FIG. 7 is a foreshortened cross sectional diagram of the cannulated screw 6 of FIG. 6 engaging the bone cortex 42.

At this point, the surgeon can exercise an option at step 118 to use a jig in accordance with well-known techniques to locate the more distal securing hole 32A. Preferably, the surgeon will use a jig but the surgeon may repeat the above process to drill out from the more distal guide 10b.

If a jig is to be used, the intramedullary nail is secured to the bone with the screw at step 120. At step 122, a jig is aligned with the screw to locate the next drill position. At step 124, the surgeon drills a hole through the skin, soft tissue and bone: using the jig. At step 128, the surgeon drives a screw through the hole to secure the nail to the bone. The surgical method stops at step 140.

If a jig is not to be used, then the drill bit is positioned in the next guide 10b. This requires the surgeon to either drill through or break through the intervening guide 10a. Because the guide bodies 10a, 10b are bio-absorbable, a cannulated drill screw can be driven through the integrated guide body 10a because the guide body 10a and any fragments 15a thereof will dissolve and be absorbed by the body. Thus, the most proximal guide body 10a can be destroyed to provide the surgeon with access to the next guide body 10b. Steps 106 through 116 are then repeated for the next guide 10b. After both holes have been drilled (step 130), both screws are driven through the nail to secure the nail to the bone (step 134). The surgical method then stops at step 140.

Figure 8:
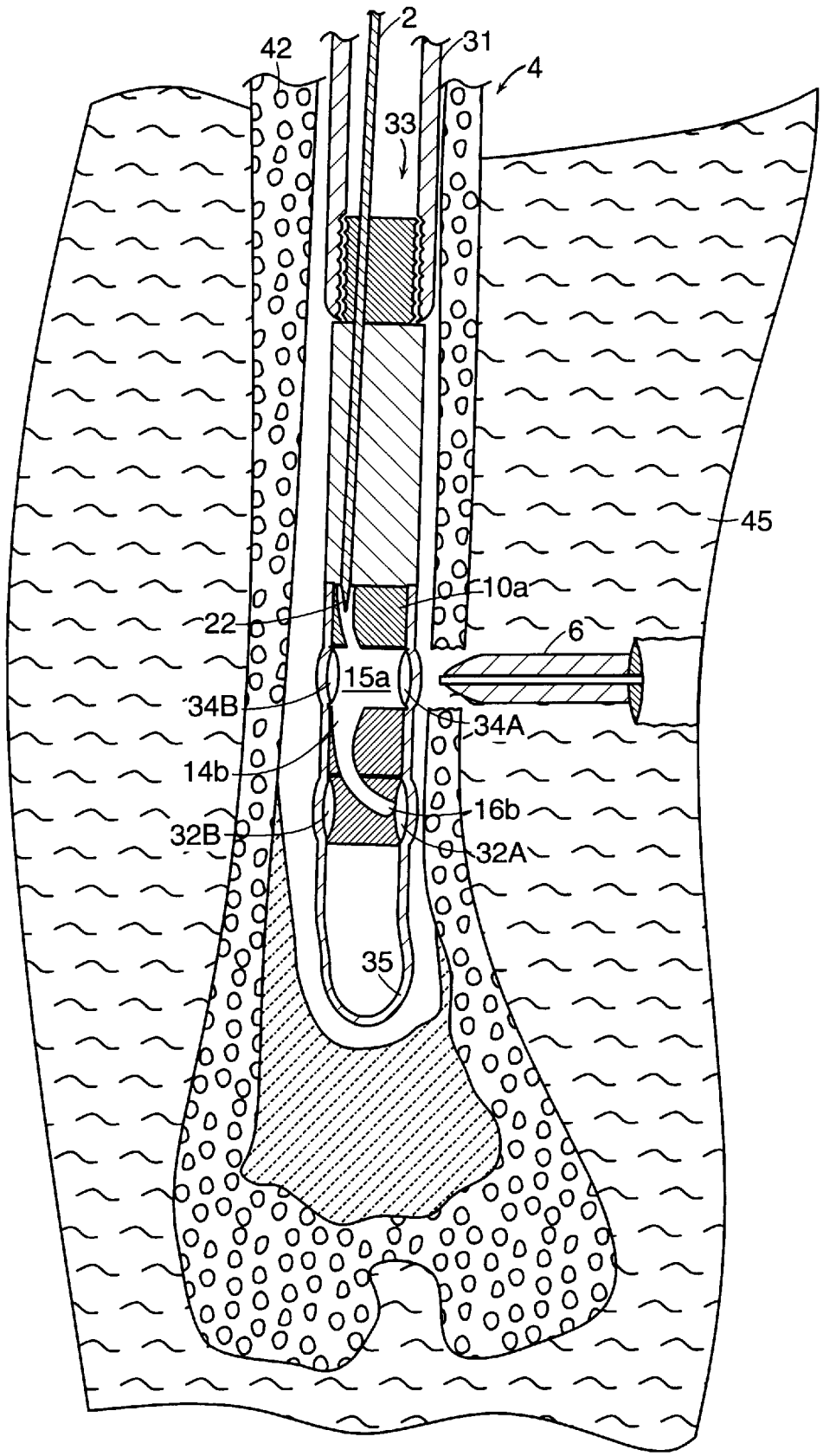
FIG. 8 is a foreshortened cross sectional schematic diagram of the integrated guide and nail apparatus of FIG. 7 with a guide being fragmented.

FIG. 8 is a foreshortened cross sectional schematic diagram view of the integrated guide and nail apparatus of FIG. 7 with the guide 10a being fragmented. Preferably, the drill screw 6 is driven through the proximal guide 10a and then extracted to the bone cortex 42 to destroy the proximal guide 10a. Because the guides 10a, 10b are fabricated from PGA, the body will absorb the fragments. The drill bit 22 can now be positioned through the fragments of the proximal guide 10a to the distal guide 10b.

Figure 9:
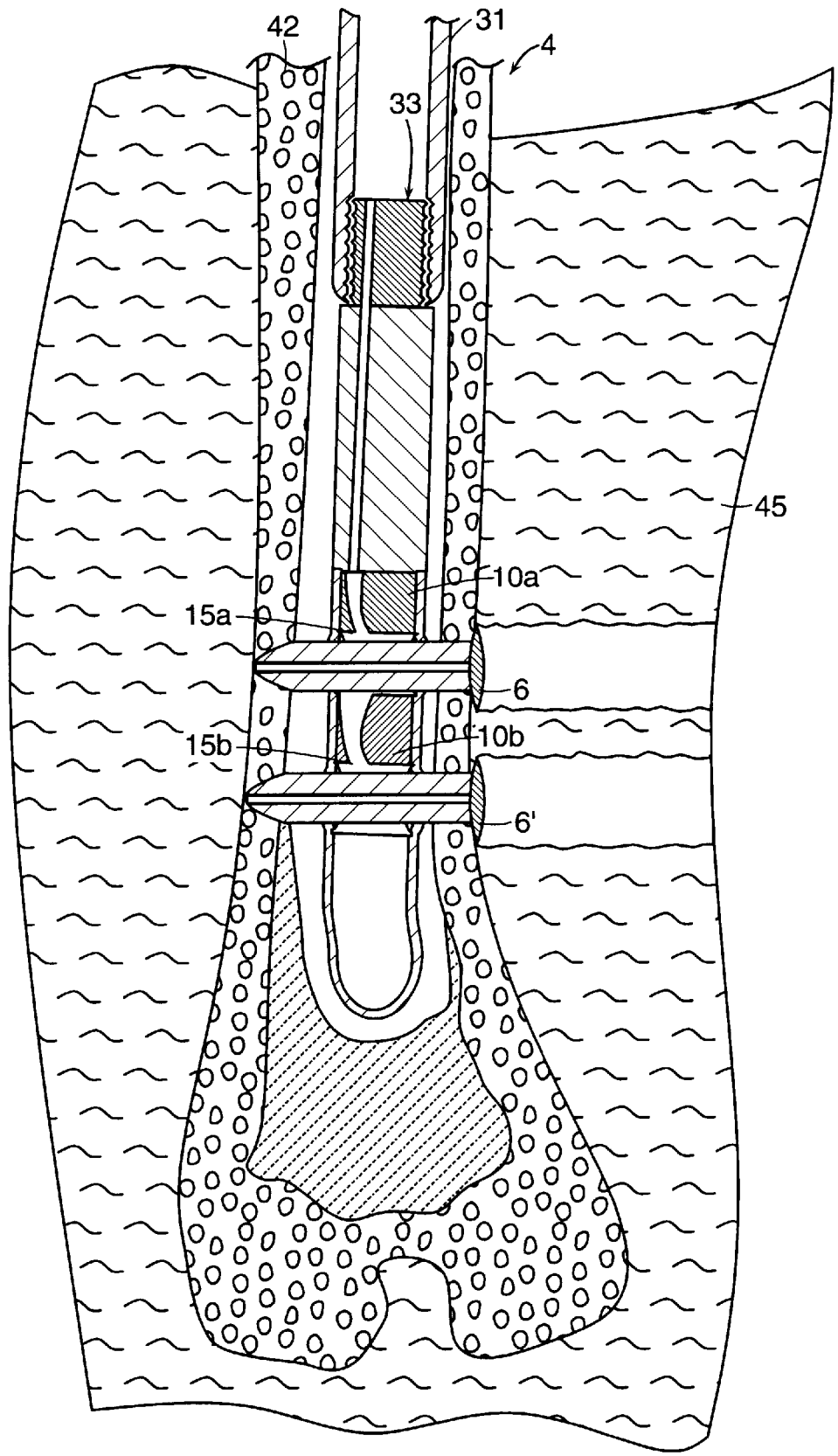
FIG. 9 is a foreshortened cross sectional schematic diagram of the nail apparatus of FIG. 1 secured to the bone.

FIG. 9 is a foreshortened cross sectional schematic diagram of the nail apparatus of FIG. 1 secured to the bone by the two screws 6, 6'. The drill shaft 2 has been removed from the nail. Both guides 10a, 10b are destroyed by the respective screws 6, 6'.

A more versatile nail tip 35 can be formed from two subsections, each of which is associated with a pair of securing holes 32A, 32B, 34A, 34B. Note that when a jig is used, the most distal pair of securing holes 32A, 32B need not be associated with a guide body 10b. Consequently, the most distal subsection can contain a distal guide body 10b or can omit the distal guide body 10b.

Although an integrated guide and nail apparatus is preferred, such an apparatus is not required to practice the system or method of the invention. By integrating the guides 10a, 10b within an intramedullary nail 3, the guides 10a, 10b are pre-aligned with the selected securing holes 32A, 34A. Alternatively, a guide can be manually aligned with the selected securing holes 32A, 34A by a surgeon. Although manual alignment increases surgical time, it may be more versatile by permitting the use of standard intramedullary nails.

Figure 10:
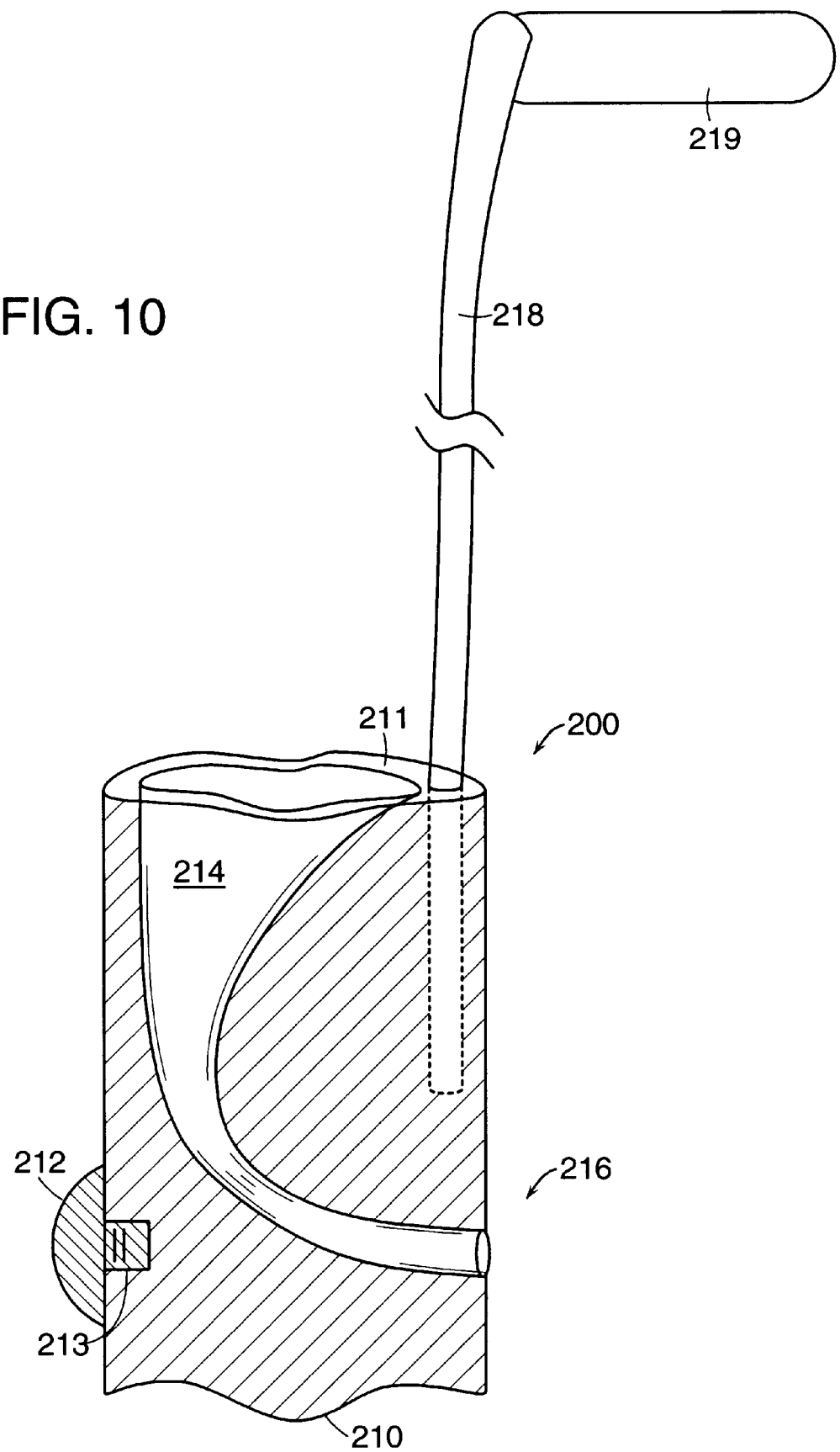
FIG. 10 is a perspective view of a manual guide apparatus partially in cross section.

FIG. 10 is a perspective view of a preferred manually-operated guide apparatus partially in cross section. The guide apparatus 200 comprises a guide body 210, a spring-loaded positioning ball detent 212, a rod 218 and a handle 219. The diameter and shape of the guide body 210 is specific to fit the lateral cross section of a particular intramedullary nail. Typical intramedullary nails have either a circular, oval, or clover-leaf cross section. The guide body 210 includes a funneling cavity 214, which has a large opening at the top surface 211 of the guide body 210. The cavity 214 leads to a smaller exit opening 216 on a lateral surface of the guide body 210 As will be described in more detail below, the cavity exit opening 216 is spaced relative to the positioning ball detent 212, such as disclosed in U.S. Pat. No. 4,781,181 to Tanguy, the teachings of which are incorporated herein by reference in their entirety. Alternatively, the positioning ball detent 212 can be cannulated, with the exit opening 216 registered to a bore through the positioning ball detent 212. The guide body 210 can be fabricated from a pliable or rigid material, including but not limited to Nylon, Delrin or stainless steel.

Figure 11:
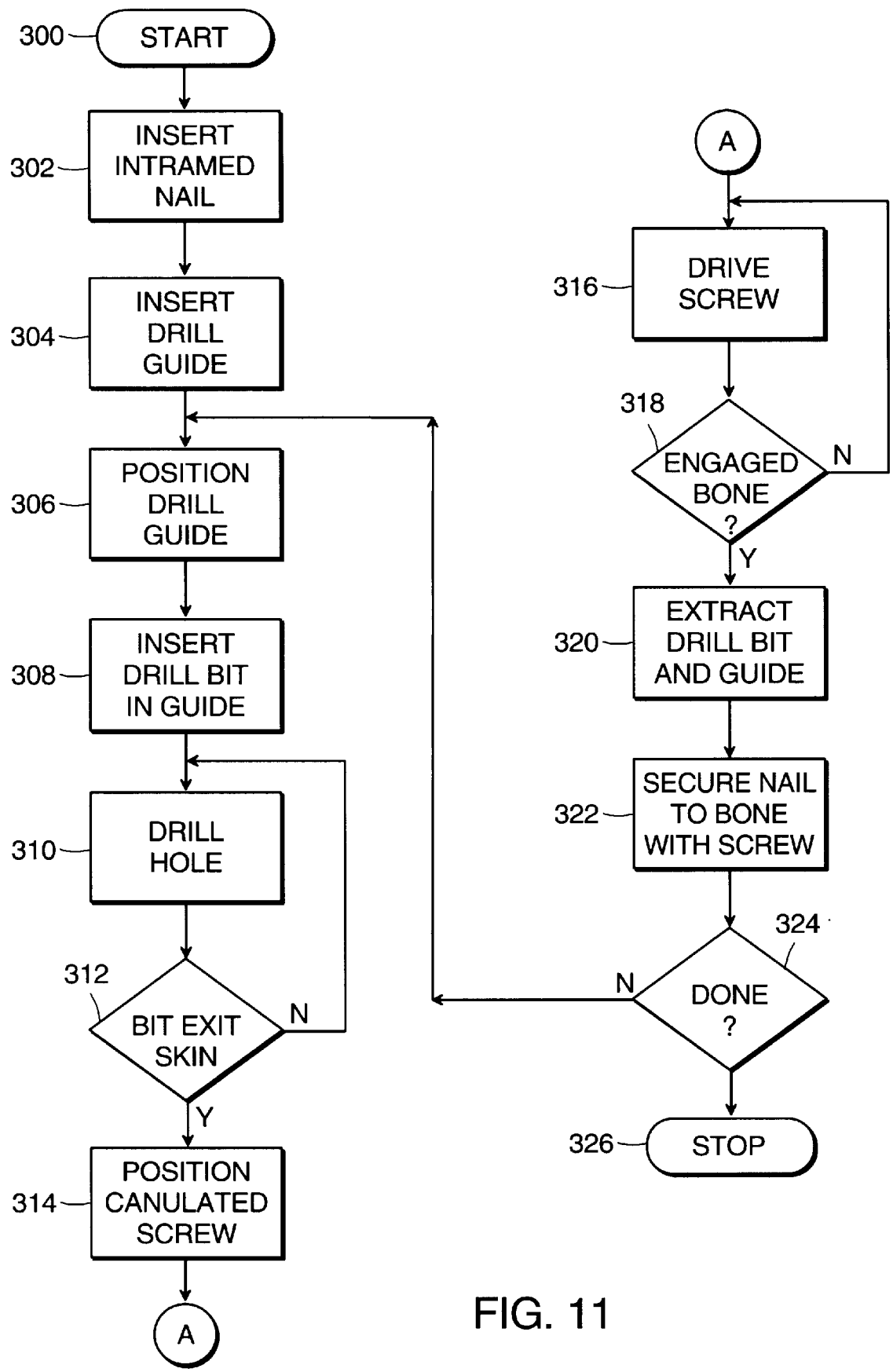
FIG. 11 is a flowchart of a preferred surgical method for using the manual guide apparatus of FIG. 10.

FIG. 11 is a flowchart of a preferred surgical method for using the guide apparatus 200 of FIG. 10. Although similar to the surgical method illustrated in FIGS. 2A–2B, the use of a guide apparatus 200 requires a different surgical method. At step 300, the surgeon begins the method after boring the intramedullary canal with any suitable technique known in the art. At step 302, an intramedullary nail 3' is inserted into the bored canal.

Figure 12:
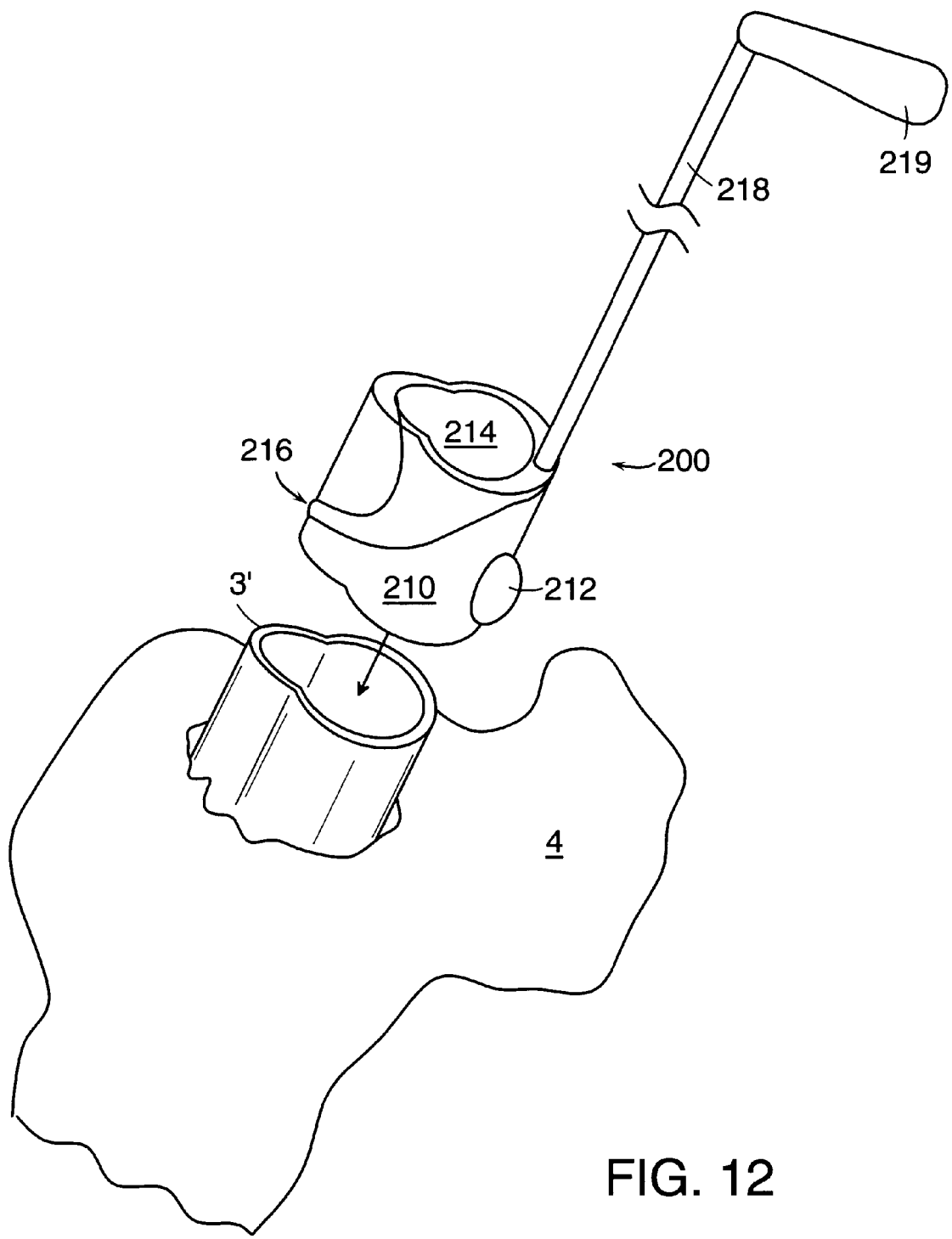
FIG. 12 is a perspective view of the guide member of FIG. 10 being inserted in a intramedullary nail.

At step 304, the surgeon inserts the drill guide apparatus 200 into the intramedullary nail. FIG. 12 is a perspective view of the guide apparatus 200 of FIG. 10 being inserted into the intramedullary, nail 3'. The guide body 210 is shaped to register with the internal cross sectional shape of the nail 3'. The surgeon inserts the guide body 210 in the direction of the arrow shown using the handle 219.

Figure 13:
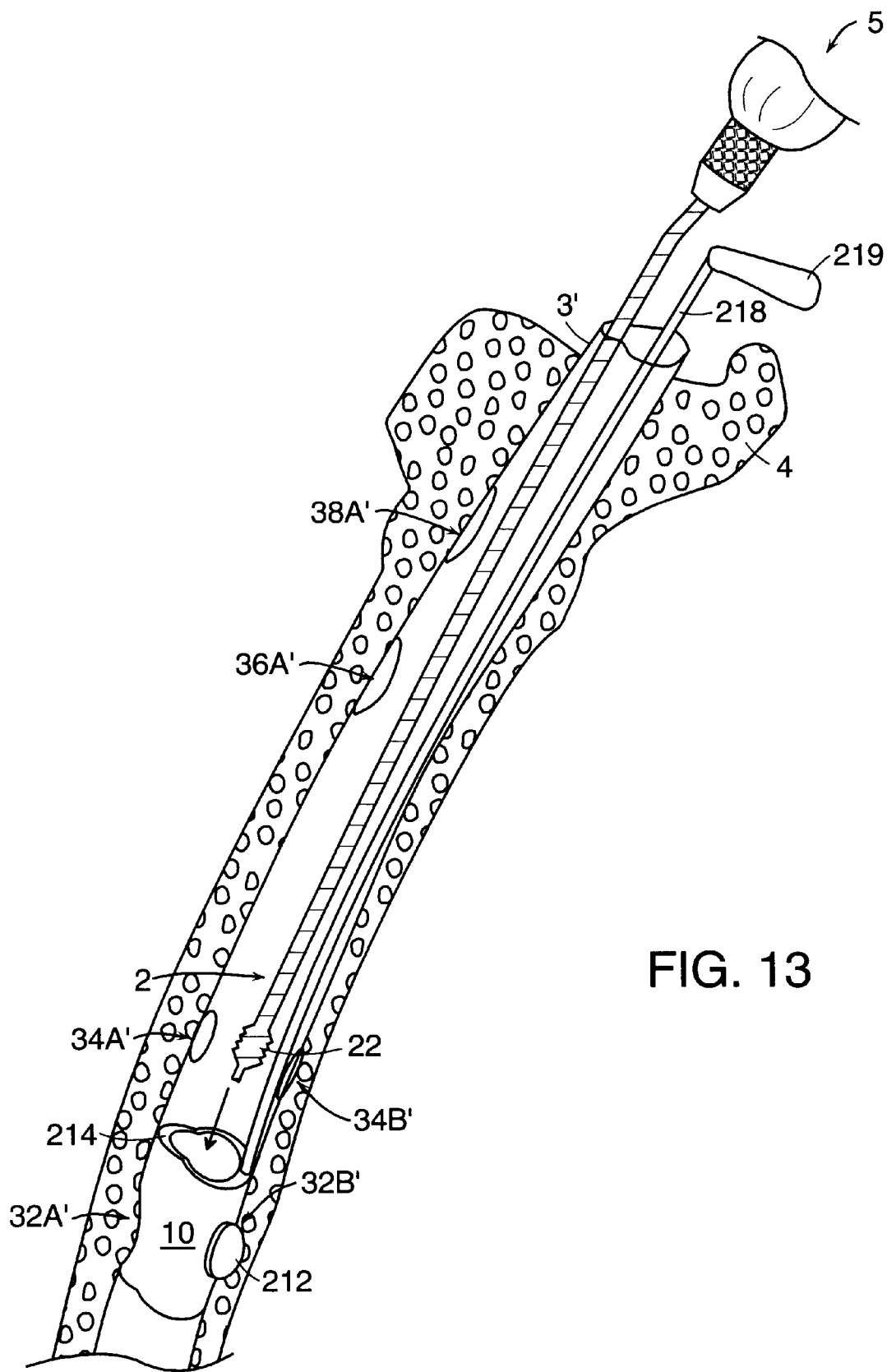
FIG. 13 is a schematic diagram partially in section of the guide apparatus of FIG. 10 registered to a securing hole.

At step 306 of FIG. 11, the surgeon operates the handle 219 to position the guide apparatus 200 at a selected interlocking securing hole in the intramedullary nail 3'. Initially, the securing hole will be at the distal end of the nail. FIG. 13 is a schematic diagram partially in section of the drill guide registered to a preformed securing hole 32A' of the intramedullary nail 3'. As illustrated, the spring-loaded positioning ball detent 212 protrudes through the located securing hole 32B'. Typically, a companion securing hole 32A' is located 180° relative to the located securing hole 32B'. As such, the exit opening 216 of the funnel cavity 214 is registered with the selected securing hole 32A'.

At step 308, the surgeon passes cl flexible speed drill bit into the funnel cavity 214 in the guide body 210. At steps 310 and 312, the surgeon attaches the speed drill bit to a power handle and drills radially out through the cortex of the bone and soft tissue of the body (e.g., lateral thigh or lower leg). As illustrated in FIG. 13, a drill shaft 2 has been secured to a power drill 5 and the drill bit 22 is fed into the funnel cavity 214 as shown by the arrow. The surgeon continues to drill until the drill bit exits the patient's skin. The drill bit 22 is now ready to receive a cannulated drill screw.

At step 314 of FIG. 11, the surgeon makes a small opening with a scalpel and places a cannulated drill screw over the speed drill bit and attaches a power drive mechanism to the drill screw.

At step 316, the cannulated drill screw is driven through the soft tissue to the bone following the flexible drill shaft. The surgeon then begins to drive the screw through the lateral cortex of the bone. After the drill screw engages the bone (step 318) but before the nail is engaged, the surgeon removes the drill shaft 2 and guide body 210 from the path of the drill screw (step 320). Alternatively, the rod 218 can be disengaged from the guide body 210 and the drill screw 6 can be driven through a preferred channel in the guide body 210.

At step 322, the surgeon completes driving the drill screw through the lateral bone, the paired securing holes of the intramedullary nail, and opposite bone cortex.

Figure 14:
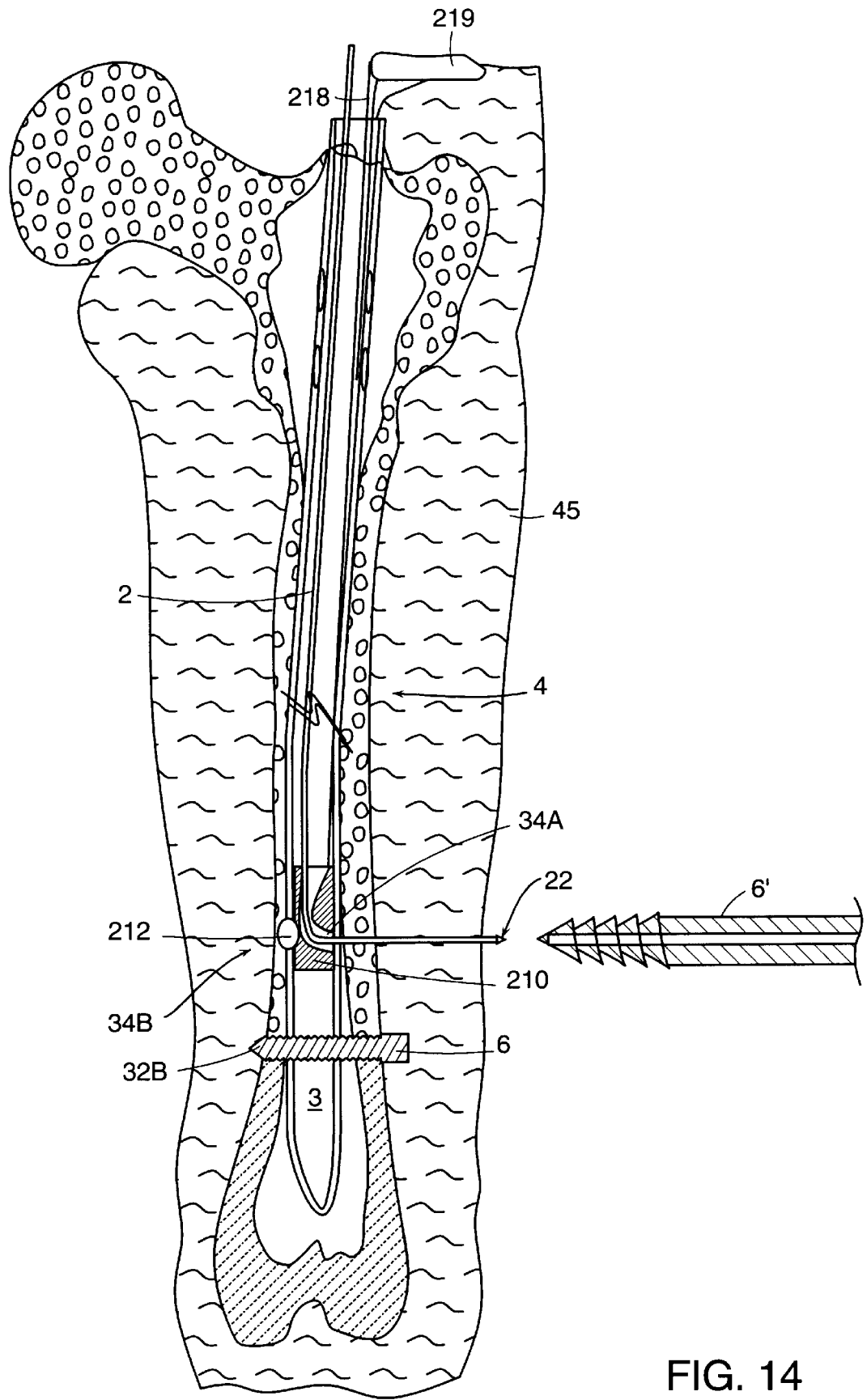
FIG. 14 is a cross sectional schematic diagram of the guide apparatus of FIG. 10 registered to a subsequent securing hole.

At step 324, if all the distal securing holes have been screwed through then the procedure terminates at step 326. Otherwise the surgeon returns to step 306 to reposition the guide apparatus 210 at the next (i.e., more proximate) securing hole. FIG. 14 is a cross sectional schematic diagram of the guide apparatus 210 of FIG. 10 registered to a subsequent securing hole 34A. The procedure followed for a second cannulated screw 6' is identical to that described above.

In the embodiments disclosed above, the flexible drill shaft must be flexible enough to be bent and directed by the cavity of the guide apparatus. At the same time, the drill shaft must be rigid enough to bore through bone cortex and soft tissue along the trajectory established by the cavity. For the surgical method to be successful, the drill shaft must pierce the patient's skin at a point on the line extending through the selected securing hole and the respective companion hole. Suitable commercially available drill shafts typically have a tightly-wounded wire coil shaft.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. An intramedullary nail having at least one pair of securing holes, comprising:
    at least one guide member integrally attached within the nail and registered to a selected securing hole of a pair of securing holes, the guide member having a cavity with an entry opening within the nail and exit opening at the selected securing hole.

2. The nail of claim 1 wherein the at least one guide member is fabricated from a bio-absorbable material.

3. The nail of claim 2 wherein the bio-absorbable material is polyglycolic acid.

4. The nail of claim 1 wherein the cavity is funnel shaped from the entry opening to the exit opening.

5. The nail of claim 1 wherein the at least one guide member is disposed at the distal end of the nail.

6. The nail of claim 5 wherein the distal end of the nail is removably coupled to a nail body.

7. An intramedullary nail having at least one pair of securing holes positioned at the distal end of the nail, comprising:
    at least one bio-absorbable guide member fixed within the nail and registered to a selected securing hole of a pair of securing holes, the guide member having a cavity with an entry opening within the nail and exit opening at the selected securing hole, the entry opening to receive an elongate member and the cavity shaped to guide the elongate member from the entry opening through the exit opening.

8. The nail of claim 7 wherein the at least one guide member is fabricated from polyglycolic acid.

9. The nail of claim 7 wherein the cavity is funnel shaped from the entry opening to the exit opening.

10. The nail of claim 7 wherein the distal end of the nail is removably coupled to a nail body.

11. An intramedullary nail, comprising:
a nail body;
a nail tip coupled to the distal end of the nail body and having at least one pair of securing holes; and
at least one guide member integrally attached within the nail tip and registered to a selected securing hole of a pair of securing holes, the guide member having a cavity with an entry opening within the nail and exit opening at the selected securing hole.

12. The nail of claim 11 wherein the at least one guide member is fabricated from a bio-absorbable material.

13. The nail of claim 12 wherein the bio-absorbable material is polyglycolic acid.

14. The nail of claim 11 wherein the cavity is funnel shaped from the entry opening to the exit opening.

15. A system for fastening an intramedullary nail having preformed securing holes in a bone of a patient, the system comprising:
an intramedullary nail;
an elongate member extendable from within the intramedullary nail, through a selected securing hole and through the skin of the patient to the outside of the patient's body; and
a fastener registered to the extending elongate member, the fastener constructed to be guided by the elongate member from the outside of the patient's body to the selected securing hole through the cortex of the bone.

16. The system of claim 15 wherein the elongate member is a drill shaft.

17. The system of claim 16 wherein the drill shaft is flexible over a portion of its length.

18. The system of claim 15 further comprising a guide member disposed within the intramedullary nail to direct the elongate member to the selected securing hole.

19. The system of claim 18 wherein the guide member includes a positioner to register the guide member with the selected securing hole.

20. The system of claim 18 wherein the guide member includes a cavity to direct the elongate member from within the intramedullary nail to the selected securing hole.

21. The system of claim 18 further comprising a manual control for manual operation and manipulation of the guide member within the intramedullary nail.

22. The system of claim 18 wherein the guide member is fixed to the intramedullary nail.

23. The system of claim 15 wherein the fastener is cannulated to receive the elongate member.

24. A system for fastening an intramedullary nail to a bone of a patient, the system comprising:
an intramedullary nail;
a guide member disposable within the intramedullary nail and registerable to a selected securing hole in the intramedullary nail;
an elongate member extendable from the guide member through the selected securing hole to pierce through the skin of the patient; and
a fastener registerable to the extending elongate member, the fastener constructed to be guided by the elongate member from outside of the patient's body to the selected securing hole through the cortex of the bone for fastening the intramedullary nail to the bone through the selected securing hole.

25. The system of claim 24 wherein the elongate member is a drill shaft.

26. The system of claim 23 wherein the guide member includes a positioner to register the guide member with the selected securing hole.

27. The system of claim 23 wherein the guide member includes a cavity to direct the elongate member from within the intramedullary nail to the selected securing hole.

28. The system of claim 23 further comprising a manual control to facilitate user operation and manipulation of the guide member while inside the intramedullary nail.

29. The system of claim 28 wherein the manual control includes a handle.

30. The system of claim 23 wherein the guide member is fixed to the intramedullary nail.

31. The system of claim 23 wherein the fastener is cannulated to receive the elongate member.

32. The system of claim 23 wherein the guide member has a circular cross section.

33. The system of claim 23 wherein the guide member has a clover-leaf cross section.

34. The system of claim 23 further comprising a drive mechanism coupled to the elongate member to extend the elongate member from within the intramedullary nail through the skin.

35. A method of fastening a intramedullary nail having preformed securing holes to a bone of a patient, comprising the steps of:
selecting a securing hole of the intramedullary nail;
registering an elongate member with the selected securing hole from within the intramedullary nail;
extending the elongate member through the skin of a patient from within the intramedullary nail;
registering a fastener to the extending elongate member; and
guiding the fastener along the elongate member from outside of the patient's body to the selected securing hole through the cortex of the bone.

36. The method of claim 35 wherein the step of registering the elongate member includes guiding the elongate member to the selected securing hole.

37. The method of claim 35 wherein the step of registering the elongate member includes positioning a guide member within the intramedullary canal.

38. The method of claim 37 wherein the step of positioning includes manually controlling the guide member.

39. The method of claim 35 wherein the step of registering the fastener includes fitting a cannulated fastener around the extending elongate member.

40. A method of fastening an intramedullary nail having securing holes to a bone of a patient, comprising the steps of:
selecting a securing hole of the intramedullary nail;
disposing a guide member within the intramedullary nail;
registering the guide member to the selected securing hole;
extending an elongate member from the guide member through the selected securing hole to pierce the skin of the patient;
registering a fastener to the extending elongate member;

guiding the fastener along the extending elongate member from outside the patient's body to the selected securing hole;

extracting the guide member relative to the selected securing hole; and driving the fastener through the intramedullary nail to fasten the intramedullary nail to the bone through the selected securing hole.

41. The method of claim 40 wherein the step of registering the fastener includes fitting a cannulated fastener around the extending elongate member.

42. A method of fastening an intramedullary nail having a plurality of securing holes to a bone, comprising the steps of:

selecting an intramedullary nail having a integrally attached guide member, the nail being selected in accordance with the dimensions of the bone;

positioning the nail within the bone;

using the guide member to locate a selected securing hole of the nail; and fastening the nail to the bone through the selected securing hole.

43. The method of claim 42 wherein the step of selecting a nail comprises:

selecting a nail body in accordance with the dimensions of the bone;

selecting a nail tip having a plurality of distal securing holes and an integrated guide member in accordance with the selected nail body; and coupling the nail tip to the nail body.

44. The method of claim 42 wherein the step of using the guide member comprises extending an elongate member from the guide member through the selected securing hole to pierce the skin of a patient.

45. The method of claim 42 wherein the step of fastening the nail comprises guiding a fastener from outside the bone through the selected securing hole and the guide member.

46. The method of claim 45 wherein the step of fastening the nail further comprises the step of fragmenting the guide member with the fastener.

47. An intramedullary nail having at least one pair of securing holes, comprising:

at least one guide member fabricated from a bio-absorbable material, the guide member fixed within the nail and registered to a selected securing hole of a pair of securing holes, the guide member having a cavity with an entry opening within the nail and exit opening at the selected securing hole.

48. The nail of claim 47 wherein the bio-absorbable material is polyglycolic acid.

49. The nail of claim 47 wherein the cavity is funnel shaped from the entry opening to the exit opening.

50. The nail of claim 47 wherein the at least one guide member is disposed at the distal end of the nail.

51. The nail of claim 50 wherein the distal end of the nail is removably coupled to a nail body.

52. An intramedullary nail, comprising:

a nail body;

a nail tip coupled to the distal end of the nail body and having at least one pair of securing holes; and at least one guide member fabricated from a bio-absorbable material, the guide member fixed within the nail tip and registered to a selected securing hole of a pair of securing holes, the guide member having a cavity with an entry opening within the nail and exit opening at the selected securing hole.

53. The nail of claim 52 wherein the bio-absorbable material is polyglycolic acid.

54. The nail of claim 52 wherein the cavity is funnel shaped from the entry opening to the exit opening.

55. A method of fastening an intramedullary nail having a plurality of securing holes to a bone, comprising the steps of:

selecting a nail body in accordance with the dimensions of the bone;

selecting a nail tip having a plurality of distal securing holes and an integrated guide member in accordance with the selected nail body;

coupling the nail tip to the nail body;

positioning the nail within the bone;

using the guide member to locate a selected securing hole of the nail; and fastening the nail to the bone through the selected securing hole.

56. The method of claim 55 wherein the step of using the guide member comprises extending an elongate member from the guide member through the selected securing hole to pierce the skin of a patient.

57. The method of claim 55 wherein the step of fastening the nail comprises guiding a fastener from outside the bone through the selected securing hole and the guide member.

58. The method of claim 55 wherein the step of guiding the fastener further comprises the step of fragmenting the guide member with the fastener.

* * * * *